United States Patent [19]

Shimamura et al.

[11] Patent Number: 5,137,922
[45] Date of Patent: Aug. 11, 1992

[54] METHOD FOR INHIBITING AND TREATING INFECTION CAUSED BY INFLUENZA VIRUS

[75] Inventors: Tadakatsu Shimamura, 4-4, Nishihara-1-chome, Shibuya-ku Tokyo; Yukihiko Hara, Fujieda, both of Japan

[73] Assignees: Mitsui Norin Co., Ltd.; Tadakatsu Shimmamura, both of Tokyo, Japan

[21] Appl. No.: 504,933

[22] Filed: Apr. 5, 1990

[30] Foreign Application Priority Data

Sep. 14, 1989 [JP] Japan ................... 1-236950

[51] Int. Cl.$^5$ ............... A61K 31/05; A61K 31/045; A61K 35/78
[52] U.S. Cl. ............... 514/731; 514/738; 514/888; 424/195.1
[58] Field of Search ............ 424/195.1; 514/731, 514/738, 888

[56] References Cited

U.S. PATENT DOCUMENTS 4,613,672  9/1986  Hara .
4,673,530  6/1987  Hara .
4,840,966  6/1989  Hara et al. .
4,913,909  4/1990  Hara et al. .

FOREIGN PATENT DOCUMENTS 0374888  6/1990  European Pat. Off. .

OTHER PUBLICATIONS

CA:89:192312k "Antivircal effects of tea catechial and black tea theaflavins on plant viruses", Okada.
CA:75:85674u "Inhibitory effect of tea catechin on the infectivity of plant virus", Okada.
CA:102:92800m "Antiviral effects of flavonoids on human viruses", Kaul et al.
Tej. N. Kaul et al., *Journal of Medical Virology*, 15, pp. 71-79 (1985).
Robert H. Green, *Proceedings of the Society for Experimental Biology and Medicine*, 71, pp. 84-85 (1949).
Mikio Nakayama et al., *Letters in Applied Microbiology*, 11, pp. 38-40 (1990).

*Primary Examiner*—John W. Rollins
*Attorney, Agent, or Firm*—Frishauf, Holtz, Goodman & Woodward

[57] ABSTRACT

The effective ingredient in the inventive medicament against infection with influenza virus is tea, e.g., black tea, or a tea polyphenol as a constituent of tea including epigallocatechin gallate, epicatechin gallate, epigallocatechin, epicatechin, (+)catechin and the isomer thereof, free theaflavin, theaflavin monogallates A and B and theaflavin digallate.

17 Claims, 2 Drawing Sheets

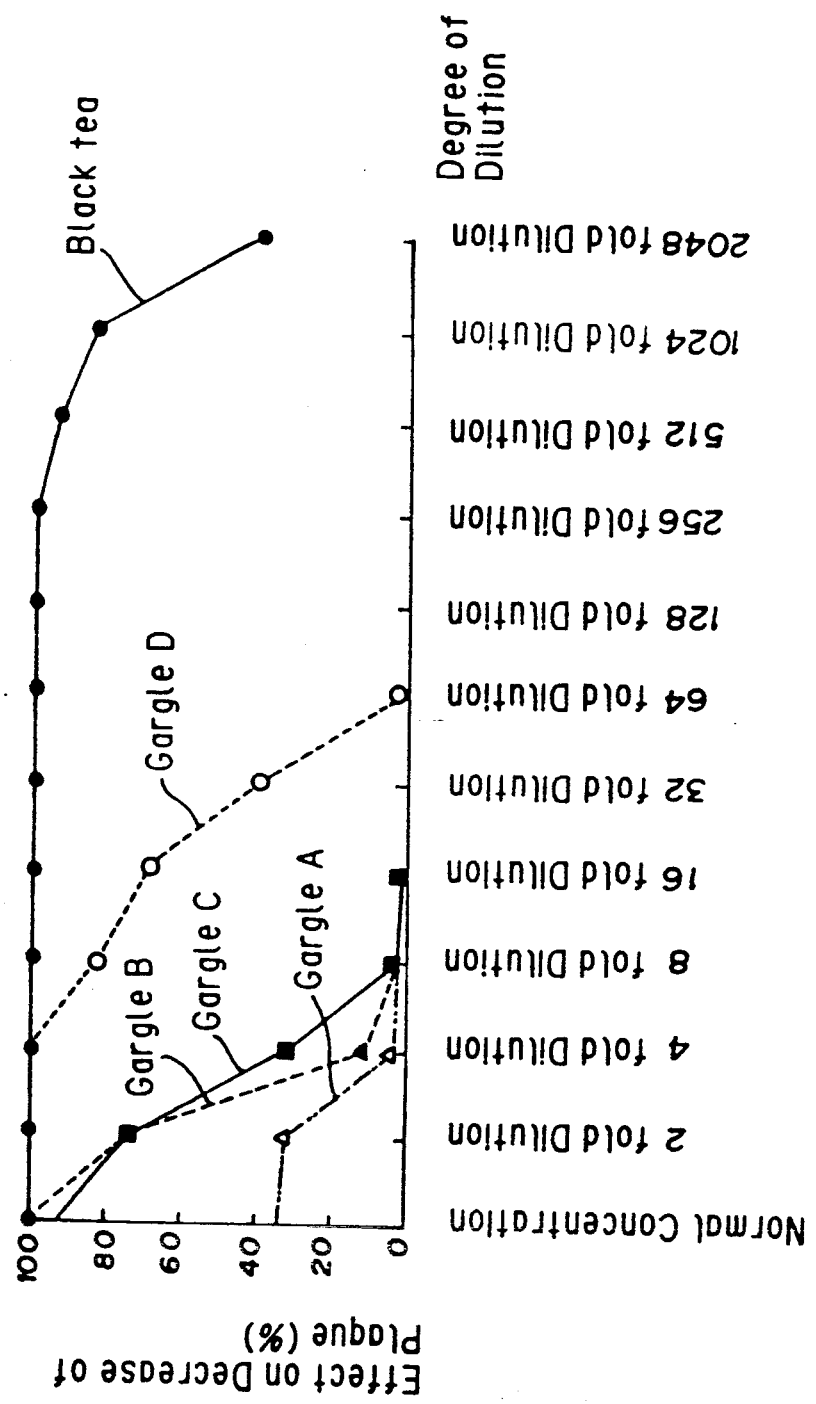

METHOD FOR INHIBITING AND TREATING INFECTION CAUSED BY INFLUENZA VIRUS

BACKGROUND OF THE INVENTION

The present invention relates to a novel preventive and curative medicament against infection with influenza virus or, more particularly, to a preventive and curative medicament against infection with influenza viruses of the type A and type B.

As is well known, influenza is an important disease of mankind which has attacked human beings periodically in the past and up to now and sometimes loads to death, e.g., more than ten million people died in one epidemic. By virtue of the great improvement in the nutrition and hygienic conditions, along with the rapid progress of the medical technology to overcome other infectious diseases in recent years, the menace by the influenza infection is no longer so great as in the past. Nevertheless, many and unspecified people are infected with the influenza viruses by airborne infection to cause one or more epidemics every year.

Many medicaments have been hitherto proposed to prevent infection with influenza viruses but none of them can exhibit fully satisfactory preventive effects. The method considered to be most effective for prevention against infection with influenza virus in these days is inoculation of vaccine. A problem in the vaccination against influenza, however, is that great difficulties are encountered, despite the relatively low probability of success, in the development works for a new influenza vaccine in order to comply with the unceasingly occurring mutation of the antigen of the influenza virus. Accordingly, it is eagerly desired to develop a novel preventive and curative medicament against infection with the influenza virus having the following properties: (1) capable of effectively exhibiting the desired preventing effect, regardless of the antigenicity of the virus and (2) usable without problems of safety due to absence of any harmful side effects against human body.

SUMMARY OF THE INVENTION

An object of the present invention is to provide a novel medicament against infection with influenza virus as mentioned above. The inventors have continued extensive investigations of natural products to discover a substance capable of exhibiting the desired effect without the problems which usually ensue in chemically synthesized compounds.

Thus, the medicament of the present invention against infection with influenza virus comprises tea as the medicinally effective ingredient.

Further, the medicament of the invention comprises polyphenol compounds in tea as the effective ingredient. The polyphenol compound in tea as the effective ingredient in the inventive medicament is selected from the group consisting of epigallocatechin gallate, epicatechin gallate, epigallocatechin, epicatechin, (+)catechin and the isomer thereof, free theaflavin, theaflavin monogallate A, theaflavin monogallate B and theaflavin digallate.

BRIEF DESCRIPTION OF THE DRAWING

FIG. 2 shows the effect on the decrease of the plaques by the antiviral activity exhibited by black tea and several commercial products of gargles as a function of ratio of dilution.

DETAILED DESCRIPTION OF THE PREFERRED EMBODIMENTS

Figure 1:
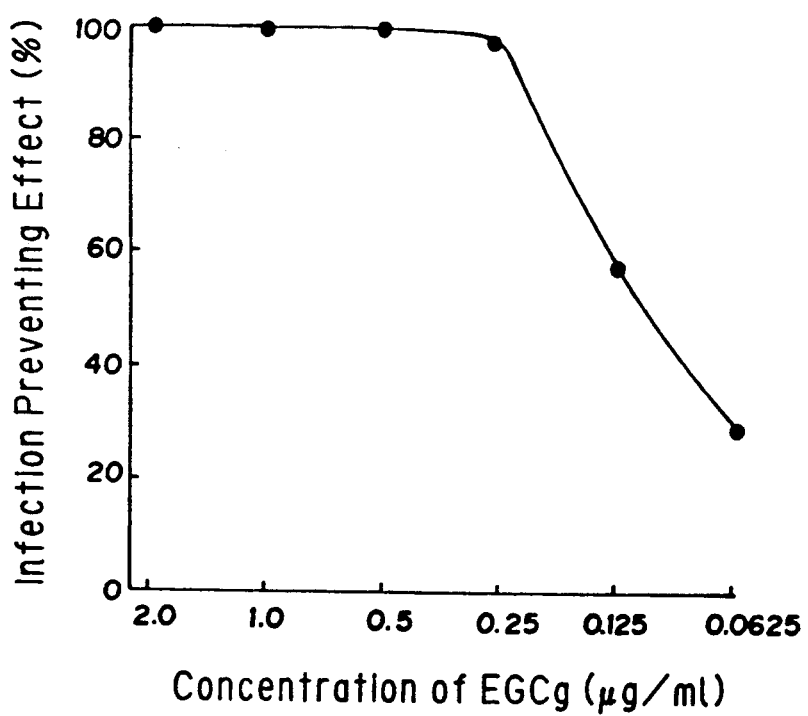
FIG. 1 is a graph showing the infection preventing effect in % as a function of the concentration of the inventive medicament.

Influenza viruses can be classified into three types of A, B and C depending on the serum types of nucleoproteins and membranous proteins. Not only human beings but also domestic fowls, pigs, horses and the like are infected with each of these three types of influenza viruses, of which the type A is the most malignant. While influenza viruses proliferate by infecting animal cells, the hemaglutinin (HA) as a glycoprotein found on the surface of the viral particles greatly participate in the initiation of infection. The hemaglutinin has an activity for cell fusion to effect fusion of the viral membrane and cell membrane so that intrusion of the viral nucleic acid into cells is facilitated to establish infection of influenza. When red blood cells are used as the target cells, agglutination of the red blood cells takes place by the activity of the hemaglutinin so that cell fusion and hemolysis are observed. On the other hand, release of the viruses through the cell membrane is controlled by the neuraminidase (NA) so that inhibition of the activity thereof also leads to prevention of viral infection.

The inventors unexpectedly have arrived at the discovery that the inventive medicament, of which the effective ingredient is tea or a tea polyphenol compound, has a power to deactivate the activity of both of the hemaglutinin and neuraminidase so that infection of cells with the influenza virus can be inhibited thereby. The inhibitive effect of infection could be confirmed, not only relative to the phenomenon of agglutination of red blood cells, but also by means of the plaque formation as a consequence of proliferation of the viruses. The infection-inhibiting effect can be exhibited by the treatment of either the viruses or the cells with the inventive medicament to give a possibility of influenza prevention. Different from vaccines, furthermore, the effectiveness of the inventive medicament is not under limitation by the antigenicity, which does not relate to the effectiveness of the inventive medicament. Namely, the present invention provides a novel preventive and curative medicament against infection with influenza viruses, of which tea is the medicinally effective ingredient.

The tea polyphenol compounds as the principal effective ingredients in the inventive medicament against infection with influenza virus include the tea catechin compounds represented by the general formula (I) given below and the theaflavin compounds represented by the general formula (II) given below:

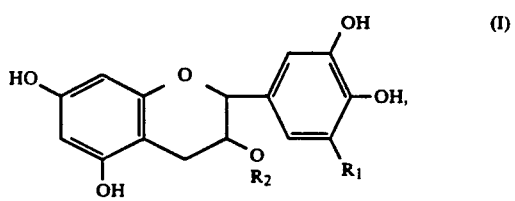

(I)

in which $R_1$ is a hydrogen atom or a hydroxy group and $R_2$ is a hydrogen atom or a 3,4,5-trihydroxy benzoyl group; and

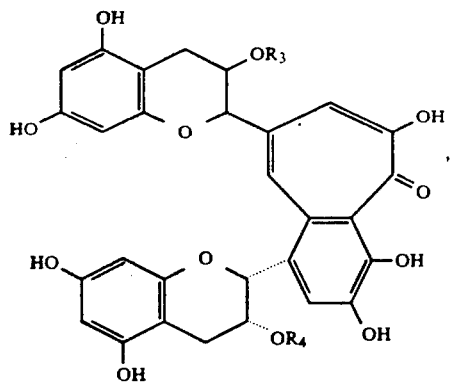

in which $R_3$ and $R_4$ are, each independently from the other, a hydrogen atom or a 3,4,5-trihydroxy benzoyl group.

Particular examples of the tea catechin compounds represented by the general formula (I) include: (−)-epicatechin, which is a compound of the formula (I) with $R_1 = H$ and $R_2 = H$; (−)-epigallocatechin, which is a compound of the formula (I) with $R_1 = OH$ and $R_2 = H$; (−)-epicatechin gallate, which is a compound of the formula (I) with $R_1 = H$ and $R_2 = 3,4,5$-trihydroxy benzoyl group; and (−)-epigallocatechin gallate, which is a compound of the formula (I) with $R_1 = OH$ and $R_2 = 3,4,5$-trihydroxy benzoyl group. Particular examples of the theaflavin compounds include: free theaflavin, which is a compound of the formula (II) with $R_3 = H$ and $R_4 = H$; theaflavin monogallate A, which is a compound of the formula (II) with $R_3 = 3,4,5$-trihydroxy benzoyl group and $R_4 = H$; theaflavin monogallate B, which is a compound of the formula (II) with $R_3 = H$ and $R_4 = 3,4,5$-trihydroxy benzoyl group; and theaflavin digallate, which is a compound of the formula (II) with $R_3 = 3,4,5$-trihydroxy benzoyl group and $R_4 = 3,4,5$-trihydroxy benzoyl group.

The above described tea polyphenol compounds can be prepared from tea leaves as the starting material and a method for the preparation thereof and a typical example of the product composition are described, for example, in Japanese Patent Kokai 59-219384, 60-13780 and 61-130285 and elsewhere.

When the inventive medicament against infection with influenza virus is prepared in a medicament form such as food, e.g., candies, collutoria, troches and the like, the tea polyphenol compounds as the effective ingredients or tea can be admixed with the medicament base either as such or as dissolved in water, alcohol and the like. An effective concentration of tea is obtained by diluting a conventional drinking tea of about 2 g/100 ml concentration by up to 260 times while the effective concentration of the tea polyphenol compounds is in the range from 1 to 100 μg/ml.

In the following, the present invention is described in more detail by way of examples conducted against type A influenza virus of the A/Sichuan/2/87(H3N2) strain and type B influenza virus of the B/USSA/100/83E strain. The medicinal agents tested include a 20 wt./vol. % extract of black tea buffered with a phosphate buffer solution, as well as epigallocatechin gallate and theaflavin digallate isolated and purified from green tea and black tea, each of which was dissolved in a phosphate buffer solution in a concentration of 1 mg/ml. The tests were conducted by further diluting the above obtained solutions.

ASSAY OF THE VIRAL ACTIVITY FOR AGGLUTINATION OF RED BLOOD CELLS

Measurements were undertaken by using 0.5% red blood cells of domestic fowls after a length of time of 1 hour.

PLAQUE MEASUREMENT

Subcultured canine kidney cells (MDCK) were used as the test cells. The culture medium for the virus proliferation was a 0.9% agar culture medium containing 2 μg/ml of trypsin, 0.4% of bovine serum albumin and the basal medium Eagle's vitamin. After infection of the cells with the virus, the culture medium was poured thereon and culturing was undertaken at 33.5° C. for 3 to 5 days. After fixation thereof with formalin, the agar was removed and the plaques were counted by dyeing with methylene blue.

OBSERVATION WITH ELECTRON MICROSCOPE

The phosphotransacetylase (PTA) dyeing method was utilized.

EXAMPLE 1

The type A influenza virus was treated for 30 minutes to 1 hour with an extract solution of black tea or epigallocatechin gallate (EGCg) and the activity for blood coagulation (hemaglutinin activity) and infectiousness (number of plaques) were examined. The results were as shown below.

Activity for serum coagulation: the activity for serum coagulation after a treatment for 30 minutes (hemaglutinin activity) was completely deactivated with a 10-fold diluted black tea.

Infectiousness (plaque counting): the number of plaques after a treatment for 1 hour was zero with each of a 2560-fold diluted black tea and 0.5 μg/ml of EGCg indicating 100% inhibition of infection.

As is shown above, infection with the virus could be inhibited by a direct treatment of the virus. FIG. 1 of the accompanying drawing shows that the hemaglutinin activity inhibiting power and the infection inhibiting power of black tea and EGCg depend on the concentration thereof.

EXAMPLE 2

Inhibition of proliferation of the type A influenza virus was examined after infection of cells. Animal cells (MDCK) infected with the virus were added to a culture medium with addition of black tea to give a concentration of 80-fold dilution or to a control culture medium without addition of black tea and culturing was performed for 48 to 96 hours.

After culturing, the supernatant was taken from each culture medium and subjected to the assay of the hemaglutinin (HA) activity. No difference could be detected by the plaque assay between the two groups in the activity of the virus at the starting moment of culturing.

The result was that the culture medium for control exhibited a HA activity of 512 after 48 hours from infection while no HA activity could be detected in the culture medium with addition of black tea in a concentration of 80-fold dilution.

EXAMPLE 3

A study was performed to examine the inhibitive power against infection with the type A influenza virus by a pretreatment of uninfected cells.

Thus, MDCK cells were treated beforehand for 1 hour with black tea or EGCg followed by infection with the virus to conduct the plaque assay. The results were that the percentage of infection inhibition was 85% with black tea in a concentration of 20-fold dilution and 45% with EGCg in a concentration of 100 µg/ml. These results support the conclusion that pretreatment of the uninfected cells is effective to inhibit infection with the influenza virus.

EXAMPLE 4

Similar experiments to Example 1 were undertaken to examine inhibition against infection with the type B influenza virus by the treatments with EGCg or theaflavin digallate (TF3) each for 1 hour in a concentration of 1 µg/ml and for 5 minutes in a concentration of 4 µg/ml. The results obtained in these four experiments were that the percentage of inhibition against infection was 100% in each. These results support the conclusion that the pretreatment of the cells is effective to inhibit infection also with the type B influenza virus.

EXAMPLE 5

A comparative study was conducted for the percentage of infection inhibiting effect with the type B influenza virus in terms of the neuraminidase (NA) activity by the determination of the isolated sialic acid by the TBA method with Fetuin as the substrate. As is summarized in the table shown below, the results were that, while the NA activity in the control test without treatment was 11, the NA activity was decreased to 8 to 2 by the treatment with black tea, epigallocatechin gallate (EGCg) or theaflavin digallate (TF3) supporting the conclusion that the treatment therewith was effective for inhibiting infection with the virus.

| Sample | NA activity |
|---|---|
| Control | 11.0 |
| Black tea, 10-fold dilution | 1.25 |
| Black tea, 20-fold dilution | 2.90 |
| Black tea, 40-fold dilution | 5.00 |
| EGCg, 50 µg/ml | 8.00 |
| EGCg, 100 µg/ml | 5.10 |
| TF3, 25 µg/ml | 3.70 |
| TF3, 50 µg/ml | 2.70 |
| TF3, 100 µg/ml | 1.70 |

EXAMPLE 6

EGCg was added to a suspension of the virus and the behavior of the virus was inspected with an electron microscope to find instantaneous formation of agglutinated lumps of the viruses indicating that EGCg had an activity as an anti-viral agent.

EXAMPLE 7

Influenza a virus was treated for 1 hour with black tea or one of the gargles (or collutoria) A, B, C and D purchased on the market in varied dilutions to examine the effect for decreasing the number of plaques for each concentration. The effective ingredients in the gargle were as follows.

A: decalinium chloride, thymol
B: popidon iodine
C: water-soluble azulene, benzetonium chloride
D: cetyl pyridinium chloride The results of the assay are shown graphically in FIG. 2 from which it is understood that, although the gargle B and D have effectiveness for inhibiting viral infection when used in a normal concentration, the effectiveness thereof is not high as compared with black tea.

The above described preventive and curative medicament against infection with influenza virus comprises, as the effective ingredient, a natural product which is a drinkable, taken in daily life in a considerably large volume so that it is absolutely free from the problem of undesirable side effects against human body, not only when it is used as a medicine, but also when it is used as an additive of food. Moreover, the effectiveness thereof is so high that infection with influenza virus can be effectively inhibited by the addition thereof even in a very low concentration to provide a means for preventing infection with influenza virus.

What is claimed is:

1. A method of inhibiting infection caused by influenza virus in humans comprising administering to a human at least one tea polyphenol extracted from tea in an amount sufficient to inhibit infection caused by influenza virus, said tea polyphenol being selected from the group consisting of epigallocatechin gallate, epicatechin gallate, epigallocatechin, epicatechin, free theaflavin, theaflavin monogallate A, theaflavin monogallate B and theaflavin digallate.

2. The method of claim 1 wherein the amount administered provides a concentration of said tea polyphenol of from 1 to 100 µg/ml.

3. The method of claim 1 wherein said tea polyphenol is epigallocatechin gallate.

4. The method of claim 1 wherein said tea polyphenol is epicatechin gallate.

5. The method of claim 1 wherein said tea polyphenol is epigallocatechin.

6. The method of claim 1 wherein said tea polyphenol is epicatechin.

7. The method of claim 1 wherein said tea polyphenol is free t flavin.

8. The method of claim 1 wherein said tea polyphenol is theaflavin monogallate A.

9. The method of claim 1 wherein said tea polyphenol is theaflavin monogallate B.

10. The method of claim 1 wherein said tea polyphenol is theaflavin digallate.

11. The method of claim 1, wherein the influenza virus is influenza virus A.

12. The method of claim 1, wherein the influenza virus is influenza virus B.

13. The method of claim 1, wherein the influenza virus is type A influenza virus of the A/Sichuan/2/87 (H3H2) strain.

14. The method of claim 1, wherein the influenza virus is type B influenza virus of the B/USSA/100/-83E/strain.

15. The method of claim 2, wherein said concentration is about 25 µg/ml.

16. The method of claim 2, wherein said concentration is about 50 µg/ml.

17. The method of claim 2, wherein said concentration is about 100 µg/ml.

* * * * *